United States Patent
Burcher

(10) Patent No.: US 8,298,144 B2
(45) Date of Patent: Oct. 30, 2012

(54) TIMING CONTROLLER FOR COMBINED PHOTOACOUSTIC AND ULTRASOUND IMAGER

(75) Inventor: Michael Burcher, Tarrytown, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 984 days.

(21) Appl. No.: 12/305,676

(22) PCT Filed: Apr. 11, 2007

(86) PCT No.: PCT/IB2007/051309
§ 371 (c)(1),
(2), (4) Date: Dec. 19, 2008

(87) PCT Pub. No.: WO2007/148239
PCT Pub. Date: Dec. 27, 2007

(65) Prior Publication Data
US 2009/0187099 A1    Jul. 23, 2009

Related U.S. Application Data

(60) Provisional application No. 60/805,625, filed on Jun. 23, 2006.

(51) Int. Cl.
*A61B 5/00* (2006.01)
*A61B 8/00* (2006.01)
(52) U.S. Cl. ...................... 600/437; 600/407
(58) Field of Classification Search .............. 600/437, 600/476, 473, 407; 367/7
See application file for complete search history.

(56) References Cited

U.S. PATENT DOCUMENTS

| 6,567,688 | B1 | 5/2003 | Wang | |
|---|---|---|---|---|
| 2005/0085725 | A1 | 4/2005 | Nagar | |
| 2005/0187471 | A1* | 8/2005 | Kanayama et al. | 600/437 |
| 2005/0288581 | A1 | 12/2005 | Kapur | |
| 2007/0299341 | A1* | 12/2007 | Wang et al. | 600/443 |

FOREIGN PATENT DOCUMENTS

| DE | 10219297 A1 | 11/2003 |
|---|---|---|
| EP | 0179522 A2 | 4/1986 |
| EP | 1535575 A1 | 6/2005 |
| EP | 1561424 A1 | 8/2005 |
| WO | 2006077579 A2 | 7/2006 |
| WO | 2007072490 A1 | 6/2007 |

OTHER PUBLICATIONS

Soumekh, M. "Depth-Focused Interior Echo Imaging", IEEE Transactions on Image Processing, vol. 8, No. 11, Nov. 1999, pp. 1608-1618.

(Continued)

*Primary Examiner* — Jacqueline Cheng
(74) *Attorney, Agent, or Firm* — W. Brinton Yorks, Jr.

(57) ABSTRACT

The present disclosure is directed to a combined photoacoustic (PA) and ultrasound imaging system capable of generating PA and ultrasound images simultaneously. These images can be combined and displayed in real-time. The PA images are acquired by firing a illumination system into a sample being imaged and beamforming the received photoacoustic signals. Ultrasound images are formed by transmitting ultrasound energy into the object and beamforming the reflected signals. The present disclosure describes a timing controller to allow the illumination system and ultrasound transmissions to be timed relative to one another. This allows both modalities to operate at close to their maximum frame rates while preventing signal interference.

16 Claims, 3 Drawing Sheets

OTHER PUBLICATIONS

Manohar, S. et al "The Twente Photoacoustic Mammoscope: System Overview and Performance", Physics in Medicine and Biology, vol. 50. No. 11, pp. 2543-2557.

Niederhauser, J. J. et al "Combined Ultrasound and Optoacoustic System for Real-Time High-Contrast Vascular Imaging in Vivo" IEEE Transactions on Medical Imaging, vol. 24, No. 4, Apr. 2005, pp. 436-440.

Xu, M. et al "Universal Back-Projection Algorithm for Photoacoustic Computer Tomography", Physical Review E. vol. 71, No. 1, pp. 16705, 2005.

\* cited by examiner

TIMING CONTROLLER FOR COMBINED PHOTOACOUSTIC AND ULTRASOUND IMAGER

The present disclosure relates to systems and methods related to photoacoustic and ultrasound imaging.

Photoacoustic (PA) tomography is an emerging medical imaging modality. (see e.g. S. Manohar, A. Kharine, J. C. G. van Hespen, W. Steenbergen, and T. G. van Leeuwen, "*The Twente Photoacoustic Mammoscope: system overview and performance,*" Physics in Medicine and Biology, vol. 50, no. 11, pp. 2543-2557, June 2005; and M. Xu and L. Wang, "*Universal back-projection algorithm for photoacoustic computer tomography,*" Physical Review E, vol. 71, no. 1, pp. 16706, 2005). A short laser pulse is fired at the object of interest (for example human or animal tissue). The laser energy is absorbed by structures within the object, causing a rapid temperature increase and thermal expansion. This thermal expansion causes ultrasound waves to propagate through the object, where they are received by ultrasound transducers placed on the surface of the object. These signals can be beamformed in order to produce an image of the absorptivity of the object at the wavelength of the laser. Since the laser radiation is scattered within the object, the illumination is not strongly focused, and an image can be formed from a single laser pulse. In order to increase the signal to noise ratio, several of these images may be averaged.

Ultrasound imaging is an established medical imaging modality. Images are formed by transmitting focused pulses of ultrasound energy into the body. The pulses are reflected by boundaries between structures within the body. The reflections propagate back to the ultrasound transducer and are then beamformed to create one A-line. Each transmission is used to form one line of the ultrasound image. An ultrasound image is therefore formed by multiple transmissions.

Recently there has been an interest in performing photoacoustic imaging combined with ultrasound imaging. (see e.g. J. Niederhauser, M. Jaeger, R. Lemor, P. Weber, and M. Frenz, "*Combined Ultrasound and Optoacoustic System for Real-Time High-Contrast Vascular Imaging in Vivo,*" Ieee Transactions on Medical Imaging, vol. 24, no. 4, pp. 436-440, April 2005). So far, these systems have operated in two modes: producing either photoacoustic or ultrasound images. Although much of the hardware and processing is common to both imaging types, no system is able to accomplish both simultaneously.

There remains a need in the industry for simultaneous use of the previously disclosed imaging systems. Existing systems operate in separate modes for photoacoustic and ultrasound imaging. Using such a system, it is possible to acquire an image in photoacoustic mode and then switch to ultrasound mode to acquire an ultrasound image of the same object.

The two modes, photoacoustic and ultrasound, operate at different frame rates. For photoacoustics, the frame rate is usually limited by the repetition rate of the laser. For typical laser systems, the repetition rate may be 10 Hz, thus allowing a frame rate of 10 Hz. For certain applications, the laser firing rate may also be limited by safety considerations. For ultrasound, typically, the frame rate depends upon the time it takes for the ultrasound pulse to propagate to the deepest tissues of interest and back to the transducer. Moreover, a "dead-time" may exist between consecutive transmissions to prevent reflection interference from the previous transmission. Ultrasound frame rates are typically 60 Hz for an imaging depth of 10 cm and 128 image lines.

Currently, the two mode system has several disadvantages. The system user may be required to switch between the two modes causing delay and exhaustive inefficient labor. Furthermore, object motion may occur during the time it takes to switch between the two images. Thus, the objects are not in the same position in both images causing undesirable results. A further disadvantage is the average frame rate for each modality is reduced, since it is not operated while the imager is in the other mode.

The present disclosure provides systems and methods for generating photoacoustic images and ultrasound images in real time. In a preferred embodiment, an imaging system is disclosed having an illumination system, adapted to generate photoacoustic signals within a sample, at least a first transducer, adapted to transmit ultrasound waves, receive ultrasound signals, and receive the photoacoustic signals and a timing control unit adapted to be in communication with the illumination system and the transducer. The timing control unit is adapted to control the timing of the illumination system and timing of the transducer, such that the ultrasound waves are transmitted between the output photoacoustic signals. The illumination system can be a laser, a source of pulsed microwave frequency radiation, or a combination thereof. The transmitted ultrasound waves can be focused beams, steered plane waves, limited-diffraction beams, synthetic aperture beams, or combinations thereof. As the ultrasound waves propagate through the sample, they will be reflected, scattered, absorbed and refracted by the sample. A single transducer can be used both to transmit the ultrasound waves and to receive the ultrasound signals. In this case, the received ultrasound signals are termed pulse-echo signals. Alternatively, separate transmitting and receiving transducers can be placed on either side of the sample to generate through-transmission ultrasound signals.

In a preferred embodiment, the illumination system is a laser adapted to generate laser pulse signals. The laser energy is absorbed by the sample, generating photoacoustic signals. Typically, the ultrasound signals and the photoacoustic signals are processed to generate ultrasound images and photoacoustic images, respectively. These images can then be combined and displayed on a display system.

The timing control unit is adapted to generate multiple communication signals characterized by (i) signal A adapted to be in communication with the illumination system, (ii) signal B adapted to be in communication with a transmit beamformer; and (iii) signal C adapted to be in communication with a receive beamformer. The illumination system is characterized by an energy beam wherein the energy beam is coupled to an optical delivery system adapted to illuminate a sample, wherein the optical delivery system includes a mirror and a diverging lens adapted to increase the area of the beam to illuminate more of the sample. If the energy source is a source of pulse microwave frequency radiation, then a waveguide is used rather than an optical delivery system. The transmit beamformer is adapted to be in communication with the transducer. An exemplary system has a multiplexer (MUX) adapted to facilitate communication among the transducer, the transmit beamformer, and the receive beamformer.

The receive beamformer is adapted to store signals from the transducer and applies appropriate processing depending on how the signals were generated. The receive beamformer is adapted to store the ultrasound images and photoacoustic images in an ultrasound frame buffer and a photoacoustic frame buffer respectively, followed by combining the stored ultrasound and photoacoustic images in an image combiner, and displaying the combined image on the display system.

The timing control unit includes a counter 1 adapted to (a) be in communication with the clock, (b) be a first frequency divider that counts to a value of D1/Tc generating a first output pulse wherein a first portion of the first output pulse is delayed by delay term D3, wherein a first portion of the delayed output pulse is signal A and a second portion of the delayed output pulse is further delayed by a monostable 2 term D5 generating signal C, and (c) transmit a second portion of the first output pulse, which is delayed by a monostable 1 term D2. The timing control unit further includes a counter 2 adapted to (a) be in communication with the clock, (b) receive a first portion of delayed output pulse from monostable 1, and (c) be a second frequency divider and count to a value of D3/Tc generating a second output pulse. The timing control unit further includes, an AND gate adapted to receive (a) counter 2 output pulse and (b) a second portion of monostable 1 delayed output pulse generating signal B.

The transducer can be a single focused element, an array of elements, a microbeamformed array, a synthetic aperture array, or combinations thereof. If the transducer is the synthetic aperture array it should be adapted to form the ultrasound signals by moving the synthetic aperture array to different positions on the sample and taking a measurement at each position.

In an exemplary embodiment, an imaging system is described wherein multiple transducers are used wherein at least one is adapted to receive a portion of the ultrasound signals, at least another is adapted to transmit ultrasound waves, and at least another is adapted to receive photoacoustic signals, generating multiple sets of measurements wherein the timing control unit is adapted to be used to prevent acoustic interference between the multiple sets of measurements. The timing control unit is adapted to be programmed to generate multiple delay times such that signal interference is prevented. The timing control unit is adapted to be applied to medical imaging of vasculature, thyroid, skin, breast, limbs and any other superficial body part or combinations thereof.

The present disclosure also describes a method of generating a combined photoacoustic and ultrasound image of a sample including the steps of, programming a timing control unit adapted to communicate with (i) an illumination system adapted to generate photoacoustic signals, (ii) an ultrasound imaging means adapted to generate ultrasound waves, and (iii) a receive beamformer, illuminating a sample with the illumination system to generate photoacoustic signals, receiving the output photoacoustic signals by a signal receiving means such as the transducer then transmitting the ultrasound waves to the sample, and receiving output ultrasound signals, by the signal receiving means wherein the receiving means is in communication with the receive beamformer, which processes the signals generating photoacoustic and ultrasound images, respectively, transmitting the images to an image combiner adapted to generate a combined image, and then transmitting the combined image to a display system.

Additional features, functions and benefits of the disclosed systems and methods will be apparent from the description which follows, particularly when read in conjunction with the appended figures.

To assist those of ordinary skill in the art in making and using the disclosed systems and methods, reference is made to the appended figures, wherein.

The present disclosure describes a system and method for a timing control unit, which controls the time at which illumination system signals, adapted to generate photoacoustic (PA) signals within a sample, and ultrasound waves are fired into a medium. The timing control unit is adapted to prevent signal interference among the different acoustic signals. The system allows a combined imaging mode, whereby photoacoustic signal means (typically a laser) may fire at its maximum repetition rate, 10 Hz for example, and ultrasound waves are transmitted between the illumination system transmissions.

The timing control unit may overcome at least one of the disadvantages of the current two mode system by not requiring switching between the separate imaging modes, minimizing the time between acquisitions (and hence minimizing disruption from object motion), preventing signal interference, and allowing each modality to operate up to its optimal frame rate.

Figure 1:
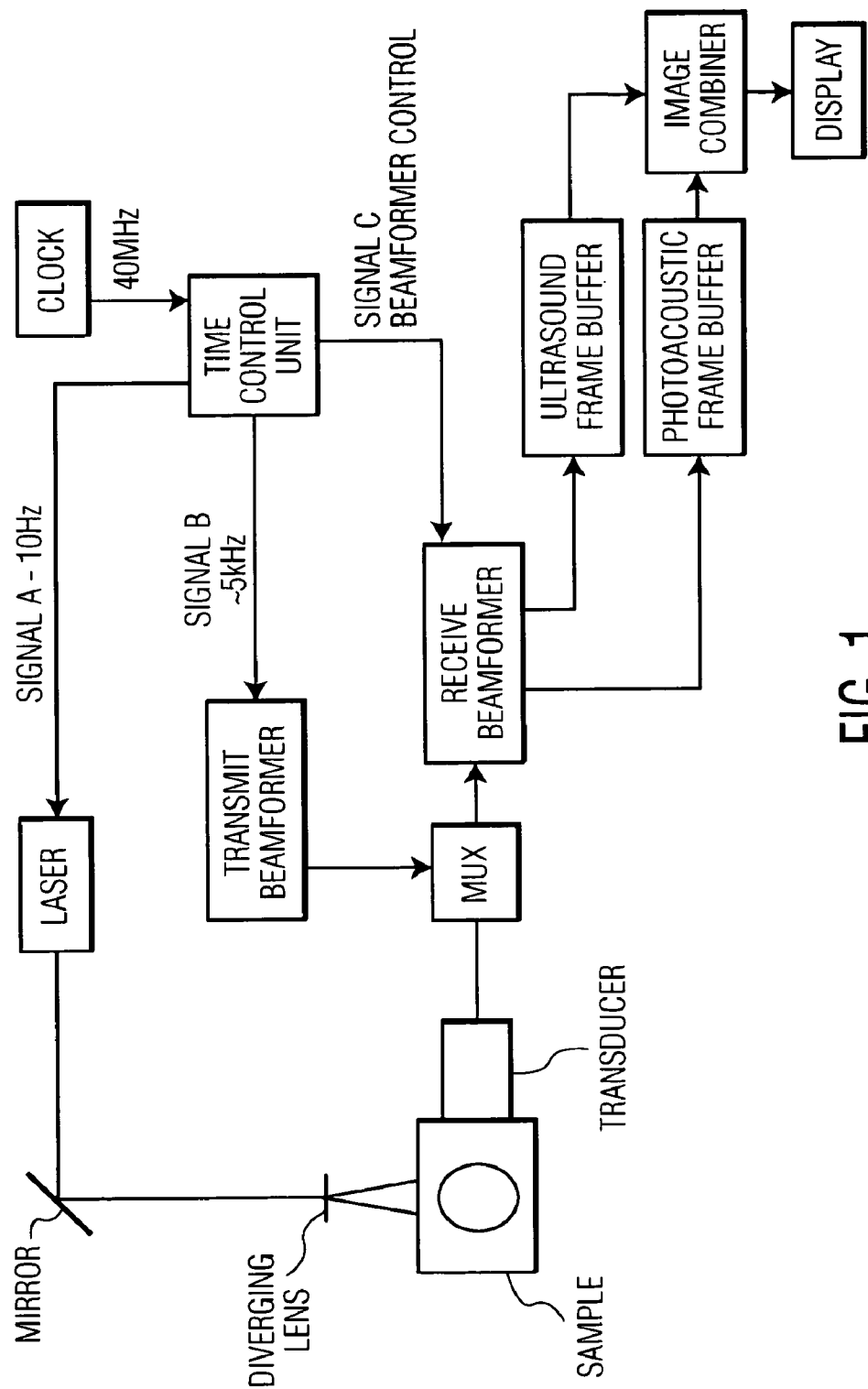
FIG. 1 is a schematic illustrating a combined imaging system.

A schematic of a preferred embodiment of the combined imaging system is shown in FIG. 1. An illumination system, typically a laser, adapted to generate photoacoustic signals within a sample, may be a Q-switched Nd:YAG laser, such as the Brilliant B manufactured by Quantel. For stable operation, preferred lasers may operate at a fixed pulse repetition rate, e.g. 10 Hz or 20 Hz. It is possible to vary the rate by a percentage of the nominal value. However, an arbitrary pulse repetition should not be set. The Q-switch of the laser is in communication with signal A generated by at least one timing control unit, thus controlling the time of the laser firing. In an exemplary embodiment, signal A can be in communication with a flash lamp of the laser. The timing control unit may also generate signal B, in communication with a transmit beamformer, and signal C in communication with a receive beamformer.

In an exemplary embodiment, the illumination system generates an energy beam, which is coupled to an optical delivery system such that the sample is illuminated. A simple optical delivery system is shown in FIG. 1 consisting of a mirror and a diverging lens. The diverging lens is capable of increasing the area of the beam, thus increasing the area of sample illumination. Illuminating the sample generates photoacoustic signals within the sample.

The timing control unit of FIG. 1 is connected to at least one clock, which provides a timing reference signal. The transmit beamformer generates electrical impulses, which are applied to a transducer. In an exemplary embodiment, a transducer has an array of piezoelectric elements, typically capable of transmitting ultrasound waves, receiving ultrasound signals and receiving PA signals. When the transmit beamformer is activated by signal B from the timing control unit, a high voltage pulse is generated. In an exemplary embodiment, the high voltage pulse signal is in communication with the piezoelectric elements of the transducer via a multiplexer, thus controlling the transducer's ultrasound transmissions. In order to focus the ultrasound wave, the transmit beamformer delays the pulse by different amounts of time on different transducer elements.

The multiplexer (MUX) of FIG. 1, typically connects the transducer to either a transmit beamformer or a receive beamformer. This may ensure that high transmit voltages are not applied to the sensitive receive circuitry of the receive beamformer. The receive beamformer stores signals from each element of the transducer and applies appropriate processing depending on how the signals were generated. In an exemplary embodiment, ultrasound signals can be pulse-echo ultrasound signals. For pulse-echo ultrasound signals, time delays are applied to per-element signals and they are then summed, forming a single A-line. The delays are calculated using the time taken for the ultrasound wave to propagate into the medium and back out again (round-trip). For photoacoustic signals, a similar delay-and-sum operation can be performed but using different time delays. Since the speed of light is much greater than the speed of sound, the laser illumination does not take a significant amount of time to penetrate the sample, and the PA signals are generated throughout the sample at the same time instant. The time delays for the photoacoustic signal therefore correspond to one-way propagation from the sample to the transducer. Alternatively, a Fourier domain reconstruction can be performed (see e.g. M. Soumekh, "*Depth-Focused Interior Echo Imaging,*" *IEEE Transactions on Image Processing*, vol. 8, no. 11, pp. 1608-1618, November 1999).

Signal C from the timing control unit is in communication with the receive beamformer. Operation of the receive beamformer can be controlled using signal C. The ultrasound and photoacoustic signals are stored in frame buffers before being combined by an image combiner and displayed on a display system.

To further illustrate the uses and advantages associated with the disclosed systems and methods, reference is made to the following examples. However, it is to be understood that such examples are not limiting with respect to the scope of the present disclosure, but are merely illustrative of exemplary implementations and/or utilities thereof:

EXAMPLE 1

Timing Control Unit Operation

In the present example, one timing control unit is used. The timing of the signals generated by a timing control unit is shown schematically below in FIG. 2. Signal A is a laser trigger control signal, signal B controls the ultrasound transmit, and signal C is the receive beamformer control signal. Signal A occurs at a specified frequency (e.g. 10 Hz: D1=100 ms). D2 is the delay between the laser trigger and the next ultrasound transmit. D2=(Time between laser trigger and illumination of sample)+(Time for ultrasound to propagate from sample to transducer)+(Photoacoustic (PA) Deadtime).

For several applications, the time between the laser trigger and the sample being illuminated will be small compared with the other timing terms, and will be ignored in the following description. In an exemplary embodiment, using a sample of dimension 10 cm and an assumed speed of sound of 1540 m/s, the time taken for the photoacoustic ultrasound pulse to propagate to the transducer=0.1 m/1540 m/s=65 μs. The PA deadtime may be required to allow ultrasonic photoacoustic reverberations within the sample to dissipate. If the deadtime is not present, then these reverberations may be received by the transducer during the subsequent pulse-echo signal and misinterpreted as part of the pulse-echo signal.

Figure 2:
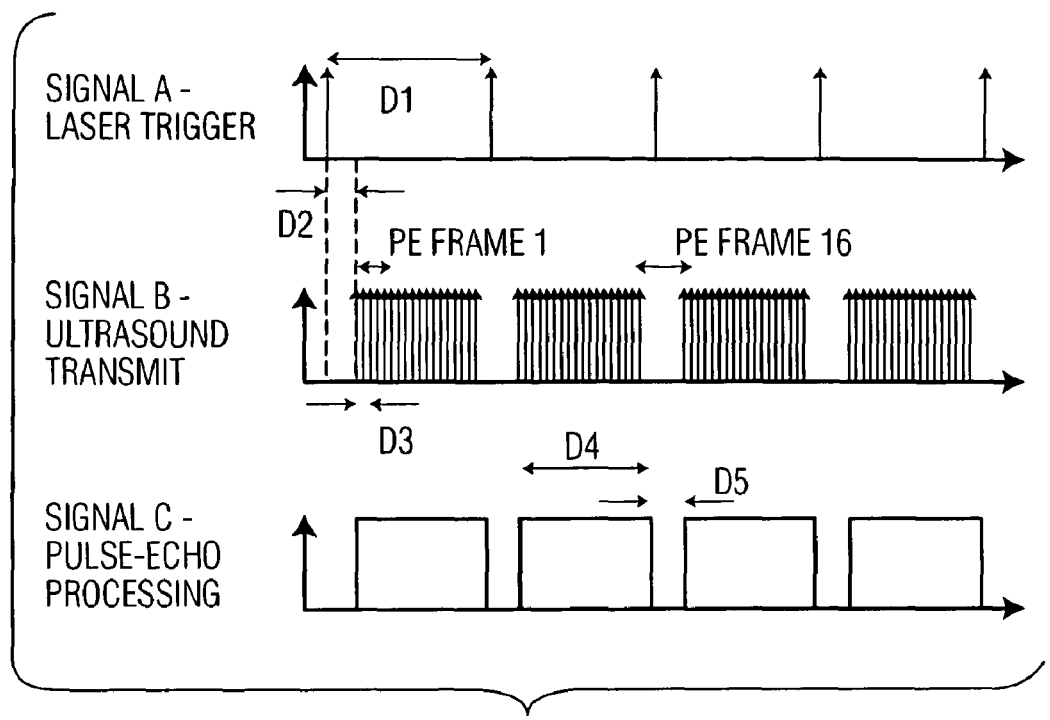
FIG. 2 is a schematic illustrating the timing of the signals generated by a timing control unit.

Signal B controls the ultrasound transmit signal. In an exemplary embodiment, the ultrasound transmit signal is a pulse-echo transmit signal. As illustrated in FIG. 2, ultrasound pulses are transmitted between laser firings, once the PA signals, generated from the illumination by the laser, have been received by the transducer (D2 complete). The time between consecutive pulse-echo transmits is D3:

D3=(Time between pulse-echo transmits)=2d/c+(Pulse-echo deadtime), where d is the maximum imaging depth, and c is the speed of sound in the sample; for example: when d=10 cm and c=1540 m/s then 2d/c=130 μs. The pulse-echo deadtime ensures that reverberations or reflections from deeper parts of the sample than the specified imaged region are not ambiguously represented within the output of the pulse-echo signal.

The number of pulse-echo signal transmits between laser pulses is determined by the expression, N_PE_transmits=floor((D1−D2)/D3). (E.g. N_PE_transmits=floor((100 ms−65 μs)/130 μs)=768). An ultrasound image, generated by the received ultrasound signals, is composed of a number of pulse-echo signal transmits, typically between 100 and 200. Therefore, several pulse echo frames can be acquired between laser pulses. Some pulse-echo frames may be interrupted by the laser pulse, as shown for pulse-echo frame 16 in FIG. 2. FIG. 2 illustrates an exemplary schematic of only a few ultrasound transmits per frame.

Signal C is the receive beamformer control signal. When signal C is low, the beamformer will perform PA processing on the received ultrasound signals. When signal C is high, the beamformer will perform pulse-echo processing on the received signals. Signal C, generated by the timing control unit, is generated such that the correct type of processing is applied to the received signals, depending on whether they are PA or pulse-echo signals. For example, it controls whether round-trip or one-way beamforming delays are used. The duration of the low signal is determined by the expression, D5=(Time for ultrasound to propagate from sample to transducer)+(PA Deadtime). (E.g. D5=65 μs). The duration of the high signal is determined by the expression, D4=D1−D5.

EXAMPLE 2

Figure 3:
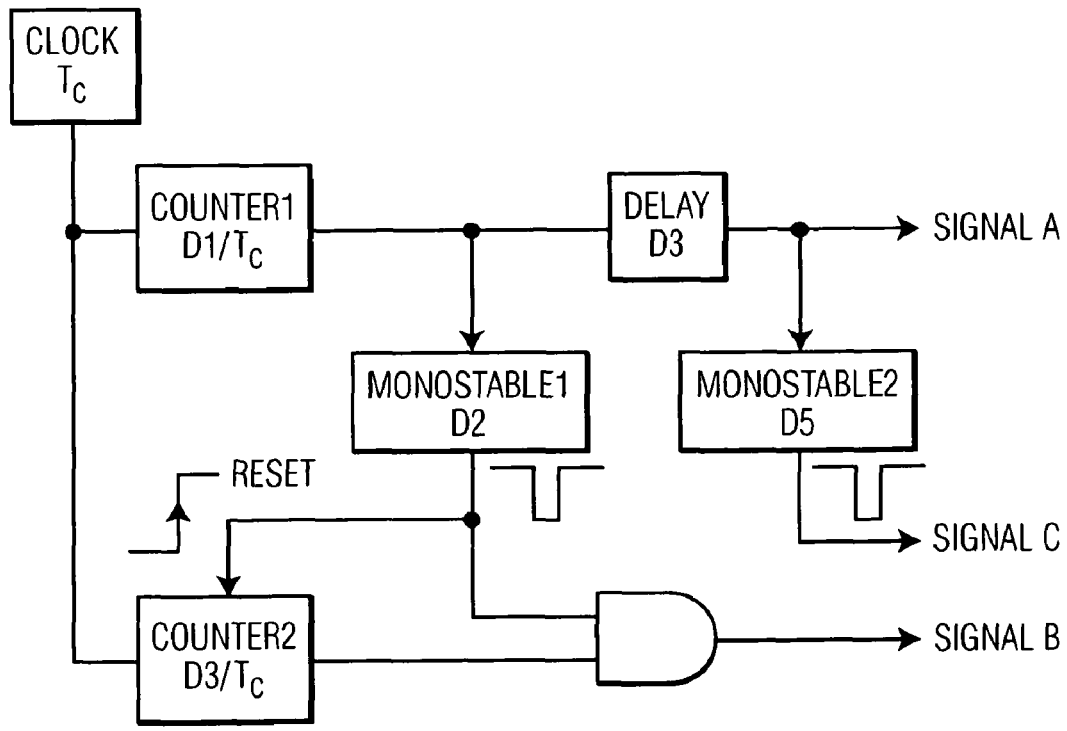
FIG. 3 is a schematic illustrating a hardware implementation of a timing control unit.
Figure 4:
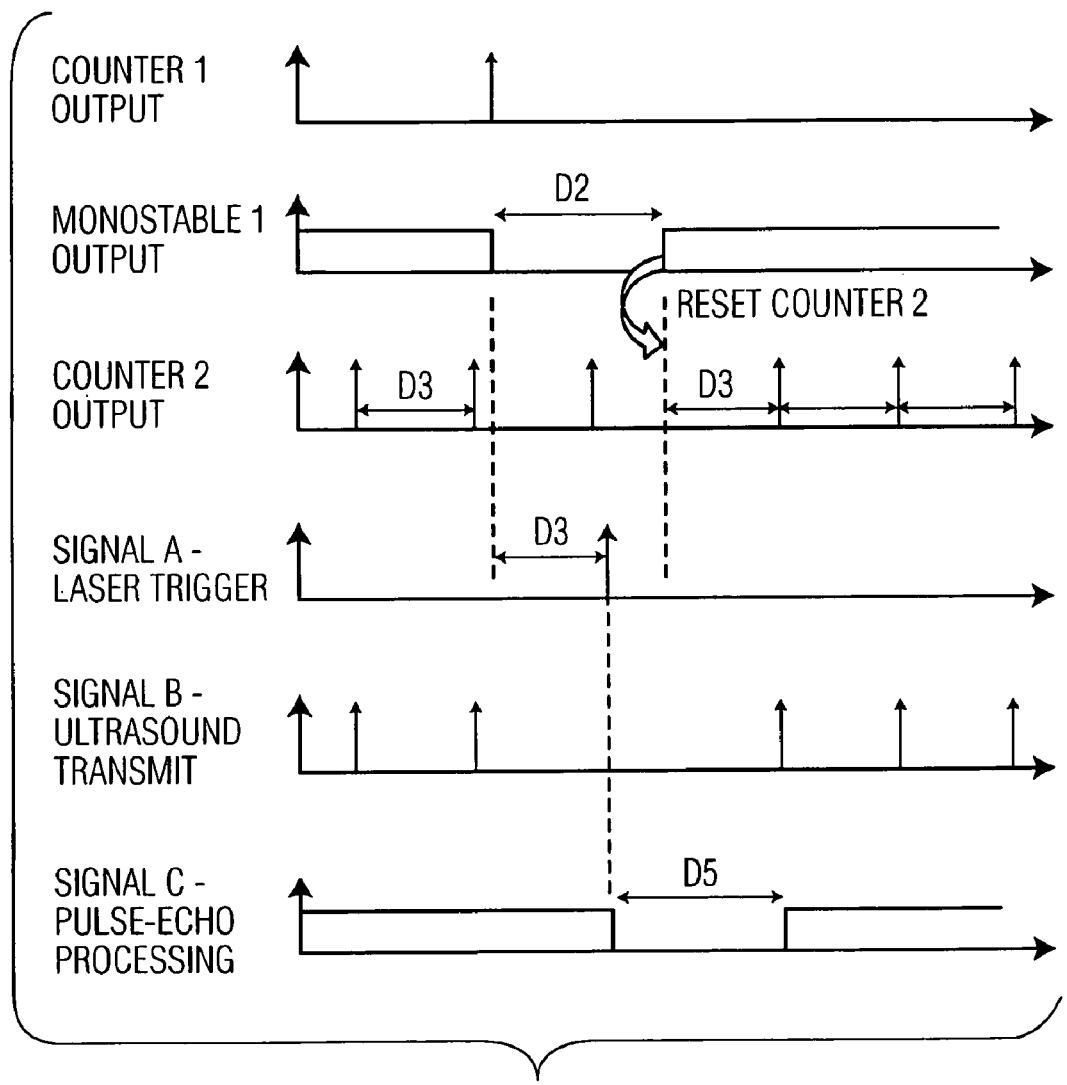
FIG. 4 is a schematic illustrating delay times of a hardware implementation of a timing control unit.

A Timing Control Unit construction is shown in FIG. 3. FIG. 4 illustrates the delay times of the hardware implementation of the timing control unit. In an exemplary embodiment, the clock has a period of about 40 MHz: Clock Time ($T_c$)=25 ns. Counter 1 acts as a frequency divider and counts to a value of $D1/T_c$, and then generates a pulse at its output. The output, therefore has a period of D1. The output signal is delayed by the delay element, which has a value of D3. This delayed signal is Signal A, the laser trigger signal.

Counter 2 also acts as a frequency divider. It counts to a value of $D3/T_c$, and then generates a pulse at its output, therefore having a period of D3. For most of the time during operation, the output of Monostable 1 is high. In the present exemplary embodiment, the output of Counter 2 will pass through an AND gate and form Signal B, thus triggering the pulse-echo transmissions having a period of D3.

When the output of Counter 1 generates a pulse, the output of Monostable 1 goes low for a duration D2 generating one input to the AND gate. As a result, signal B will be low and no ultrasound pulses will be fired. After a delay of D3 (which is sufficient time for the pulse-echo cycle to complete), signal A will be active and the laser will be triggered. After a time D2, the output of Monostable 1 will become high again. This transition resets Counter 2. Following a time D3 after the transition, signal B will fire again and the pulse-echo sequence will continue.

Monostable 2 is used to generate signal C, generating output that is high except for a time D5 after each laser trigger.

Exemplary embodiments are disclosed below to more precisely illustrate the present disclosure. It is to be understood that such examples are not limiting with respect to the scope of the present disclosure, but are merely illustrative of exemplary implementations and/or utilities thereof. They are not intended to limit the scope of the present disclosure.

The hardware described above can be implemented using standard integrated circuits, dedicated hardware (an ASIC) or a field-programmable gate array. The above timing signals can also be generated by software, for example a real-time operating system such as VxWorks. The values of the delays (D1-D5) can be made programmable. This allows them to be changed depending on the depth of imaging, speed of sound in the medium, laser parameters, etc. In addition, they can be adapted dynamically, for example varying depending on measurements of speed of sound in the medium. A source of pulsed microwave frequency radiation can be used instead of the laser or a combination of both. The ultrasound image can be formed using an alternative type of pulse transmission or a combination of the following, for example steered plane waves, limited-diffraction beams, or synthetic aperture beams. The ultrasound-only image can also be formed by through-transmission. In the present disclosure, multiple transducers can be used. In an exemplary embodiment, a first transducer can be used to transmit the ultrasound waves, and a second transducer can be used to receive the ultrasound signals.

The ultrasound transducer can be a single focused element, a microbeamformed array, or an array of elements. It may also be a synthetic aperture array, formed by moving the transducer to different positions and measuring at each position. An exemplary transducer can have an array of piezoelectric elements, or be a Capacitive micromachined ultrasonic transducer (CMUT). Signal C can be used to control other processing stages in addition to the receive beamformer. Thus, different processing can be applied to signals received from the illumination system excitation and the ultrasound pulse. For example the signals from the different sources may be filtered with different bandwidth filters.

The PA and pulse-echo measurements can be made by multiple transducers. In an exemplary embodiment a first transducer is used to receive the photoacoustic signals and a second transducer is used to receive the ultrasound signals. In an exemplary embodiment using multiple transducers, the timing control unit is further used to prevent acoustic interference between multiple sets of measurements. Ultrasound signals and photoacoustic signals must not be generated within the sample at the same, or close times.

The present disclosure can be applied in medical imaging. It can be incorporated into a combined ultrasound and photoacoustic imaging device. This can be similar in form to existing ultrasound only imaging devices, such as the Philips iU22 or iE33. It can be used for example to image the vasculature, thyroid, skin, breast, other superficial parts of the body, or combinations thereof. It can also be used during interventional procedures. The photoacoustic signal can be used to generate images of blood, or contrast agents (such as gold nanorods).

In sum, the systems and methods of the present disclosure offer significantly enhanced techniques for a combined photoacoustic and ultrasound imaging system and method.

Although the present disclosure has been described with reference to exemplary embodiments and implementations thereof, the disclosed systems and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. An imaging system, comprising:
   an illumination system adapted to illuminate a sample for generating photoacoustic signals in the sample;
   a transducer comprising an array of piezoelectric elements, and adapted to: (i) transmit ultrasound waves, (ii) receive ultrasound signals generated in response to said ultrasound waves, and (iii) receive the photoacoustic signals generated from said illumination system;
   a transmit beamformer adapted to be in communication with said array of piezoelectric elements;
   a receive beamformer adapted to: (i) receive the ultrasound signals generated in response to said ultrasound waves, (ii) receive the photoacoustic signals generated from the illumination system, (iii) apply time delays to the received ultrasound signals calculated using a round-trip propagation time of the ultrasound waves from and to the transducer, (iv) apply time delays to the photoacoustic signals calculated using a one-way propagation time of the photoacoustic signals from the sample to the transducer, (v) generate ultrasound images from the received ultrasound signals, and (vi) generate photoacoustic images from the received photoacoustic signals;
   a timing control unit adapted to be in communication with:
   (i) at least a first clock adapted to generate a time reference signal, (ii) said illumination system, and (iii) said transmit beamformer,
   wherein said timing control unit is further adapted to: (i) control a timing of said photoacoustic signals and a timing of said ultrasound waves, such that said ultrasound waves are transmitted between said photoacoustic signals and that the ultrasound signals and the photoacoustic signals are differently processed by the receive beamformer, (ii) prevent signal interference between said ultrasound signals and said photoacoustic signals, and (iii) control the delay time to the received ultrasound signals and the delay time to the photoacoustic signal.

2. A system according to claim 1 wherein said illumination system comprises an energy beam.

3. A system according to claim 2 wherein said energy beam is a laser coupled to an optical delivery system adapted to illuminate the sample, wherein said optical delivery system having a minor and a diverging lens is adapted to increase the area of said beam to illuminate more of said sample.

4. A system according to claim 2 wherein said energy beam is a source of microwave pulse frequency radiation coupled to a waveguide delivery system.

5. A system according to claim 2 further comprising a display system and wherein said ultrasound images and said photoacoustic images are combined and displayed on the display system.

6. A system according to claim 2, wherein said timing control unit is further adapted to generate multiple communication signals characterized by: (i) signal A adapted to be in communication with said illumination system, (ii) signal B adapted to be in communication with the transmit beamformer; and (iii) signal C adapted to be in communication with the receive beamformer.

7. A system according to claim 6 further comprising a multiplexer (MUX) adapted to facilitate communication among said transducer, said transmit beamformer, and said receive beamformer.

8. A system according to claim 7 wherein said receive beamformer is further adapted to store signals from each piezoelectric element of said array of piezoelectric elements of said transducer and applies appropriate processing depending on how said stored signals were generated.

9. A system according to claim 8 further comprising:
an ultrasound frame buffer adapted to store said ultrasound images;
a photoacoustic frame buffer adapted to store said photoacoustic images;
a image combiner adapted to generate a combined image;
a display system adapted to display said combined image;
wherein said receive beamformer is further adapted to transmit said stored signals to the ultrasound frame buffer and the photoacoustic frame buffer;
wherein said frame buffers are further adapted to transmit said ultrasound and photoacoustic images to the image combiner; and
wherein said image combiner is further adapted to transmit said combined image to the display system.

10. A system according to claim 6 wherein said timing control unit further includes:
a first counter adapted to: (a) be in communication with the first clock, (b) be a first frequency divider and count to a value of $D1/T_C$ (wherein D1 is a time of a signal cycle and $T_C$ is a clock time) generating a first output pulse wherein a first portion of said first output pulse is delayed by delay term D3 (wherein D3 is the time between pulse-echo transmits), and wherein a first portion of said delayed output pulse is said signal A and a second portion of said delayed output pulse is further delayed by a second monostable for a duration of D5 (wherein D5 is the time for the ultrasound wave to propagate from the sample to the transducer plus a photoacoustic deadtime) generating said signal C, and (c) have a second portion of said first output pulse delayed by a first monostable for a duration of D2 (wherein D2 is the delay between a trigger of the illumination system and a next ultrasound wave transmit);
a second counter adapted to: (a) be in communication with said first clock, (b) receive a first portion of the delayed output pulse from the first monostable, and (c) be a second frequency divider and count to a value of D3/Tc generating a second output pulse; and
an AND gate adapted to receive: (a) the second counter output pulse and (b) a second portion of the delayed output pulse from the first monostable, the AND gate generating said signal B.

11. A system according to claim 10 wherein said timing control unit is adapted to be programmed to generate multiple delay times such that signal interference is prevented.

12. A system according to claim 1 wherein said ultrasound waves takes the form of a member selected from the group consisting of focused beams, steered plane waves, limited diffraction beams, synthetic aperture beams, and combinations therein.

13. A system according to claim 1 wherein said transducer is selected from the group consisting of an array of elements, a synthetic aperture array, a microbeamformed array, and combinations thereof.

14. A system according to claim 13 wherein the transducer is selected as a synthetic aperture array and wherein said synthetic aperture array is adapted to form said ultrasound signals by moving said synthetic aperture array to different positions on said sample and taking a measurement at each position.

15. A system according to claim 1 wherein said transducer comprises multiple transducers, the multiple transducers are adapted to generate said ultrasound signals having multiple sets of measurements, and wherein said timing control unit is further adapted to prevent acoustic interference between said multiple sets of measurements.

16. A system according to claim 1 wherein said timing control unit is adapted to be applied to medical imaging of a member of the group consisting of vasculature, thyroid, skin, breast, limbs and combinations thereof.

* * * * *